(12) United States Patent
Fukuda et al.

(10) Patent No.: US 8,853,413 B2
(45) Date of Patent: Oct. 7, 2014

(54) PROCESS FOR PRODUCING PYRIPYROPENE DERIVATIVES

(75) Inventors: Yoshimasa Fukuda, Yokohama (JP);
Takashi Ando, Yokohama (JP);
Kimihiko Goto, Yokohama (JP);
Nozomu Nakanishi, Yokohama (JP);
Takashi Watanabe, Yokohama (JP);
Kenichi Kurihara, Matsuyama (JP);
Nobuto Minowa, Yokohama (JP);
Masaaki Mitomi, Yokosuka (JP)

(73) Assignee: Meiji Seika Pharma Co., Ltd., Tokyo-To (JP)

( * ) Notice: Subject to any disclaimer, the term of this patent is extended or adjusted under 35 U.S.C. 154(b) by 42 days.

(21) Appl. No.: 13/266,671

(22) PCT Filed: May 12, 2010

(86) PCT No.: PCT/JP2010/058040
§ 371 (c)(1),
(2), (4) Date: Oct. 27, 2011

(87) PCT Pub. No.: WO2010/131676
PCT Pub. Date: Nov. 18, 2010

(65) Prior Publication Data
US 2012/0046470 A1    Feb. 23, 2012

(30) Foreign Application Priority Data
May 13, 2009  (JP) .................................. 2009-116305
Mar. 1, 2010  (JP) .................................. 2010-044416

(51) Int. Cl.
*C07D 401/04*  (2006.01)

(52) U.S. Cl.
USPC ...................................................... 546/283.1

(58) Field of Classification Search
USPC ...................................................... 546/283.1
See application file for complete search history.

(56) References Cited

U.S. PATENT DOCUMENTS

| | | |
|---|---|---|
| 5,807,721 A | 9/1998 | Omura et al. |
| 2006/0281780 A1 | 12/2006 | Goto et al. |
| 2010/0160640 A1 | 6/2010 | Goto et al. |
| 2010/0281584 A1 | 11/2010 | Horikoshi et al. |
| 2011/0195998 A1 | 8/2011 | Goto et al. |

FOREIGN PATENT DOCUMENTS

| | | |
|---|---|---|
| CN | 101188937 | 5/2008 |
| EP | 2 107 060 | 10/2009 |
| EP | 2 186 815 | 5/2010 |
| JP | 06-184158 | 7/1994 |
| JP | 8-239385 | 9/1996 |
| JP | 8-259569 | 10/1996 |
| JP | 8-269065 | 10/1996 |
| WO | 94/09147 | 4/1994 |
| WO | 2004/060065 | 7/2004 |
| WO | 2006/129714 | 12/2006 |
| WO | 2008/066153 | 6/2008 |
| WO | 2009/022702 | 2/2009 |
| WO | 2009/081851 | 7/2009 |
| WO | 2011/108155 | 9/2011 |

OTHER PUBLICATIONS

International Search Report issued Jul. 13, 2010 in International (PCT) Application No. PCT/JP2010/058040 of which the present application is the national stage.
R. Obata et al., Chemical Modification and Structure-activity Relationships of Pyripyropenes, 1. Modification at the Four Hydroxyl Groups, The Journal of Antibiotics, vol. 49, No. 11, pp. 1133-1148, 1996.
R. Obata et al., Chemical Modification and Structure-activity Relationships of Pyripyropenes; Potent, Bioavailable Inhibitor of Acyl-CoA: Cholesterol O-Acyltransferase (ACAT), Bioorganic & Medicinal Chemistry Letters, vol. 5, No. 22, pp. 2683-2688, 1995.
R. Obata et al., Chemical Modification and Structure-activity Relationships of Pyripyropenes, 2. 1,11-Cyclic Analogs, The Journal of Antibiotics, vol. 49, No. 11, pp. 1149-1156, 1996.
R. Obata et al., Structure-activity Relationships of Pyripyropenes Fungal Acyl-CoA: Cholestetol Acyltransferase Inhibitors, The Journal of Antibiotics, vol. 48, No. 7, pp. 749-750, 1995.
European Search Report issued Dec. 20, 2011 in corresponding European Application No. 10 77 4933.
R. Obata et al., "Chemical Modifications and Structure-activity Relationships of Pyripyropenes., 1. Modification at the Four Hydroxyl Groups", The Journal of Antibiotics, vol. 49, No. 11, pp. 1133-1148, 1996.

(Continued)

Primary Examiner — Patricia L Morris
(74) Attorney, Agent, or Firm — Wenderoth, Lind & Ponack, L.L.P.

(57) ABSTRACT

Disclosed is a process for efficiently producing pyripyropene derivatives having acyloxy at the 1-position and 11-position and hydroxyl at the 7-position. The process comprises selectively acylating hydroxyl at the 1-position and 11-position of a compound represented by formula B1 through one to three steps with an acylating agent in the presence or absence of a base.

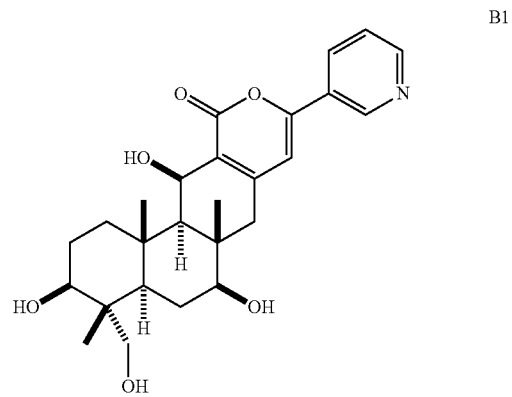

12 Claims, 1 Drawing Sheet

(56) References Cited

OTHER PUBLICATIONS

International Preliminary Report on Patentability and Written Opinion issued Dec. 12, 2011 in International (PCT) Application No. PCT/JP2010/058040, of which the present application is the national stage.

Shiomi et al., "Meroterpenoids with various biological activities produced by fungi", Pure Appl. Chem., vol. 71, No. 6, pp. 1059-1064, 1999.

Sunazuka et al., "Synthetic Study of α-Pyrone Meroterpenoids, Pyripyropens", Journal of Synthetic Organic Chemistry, vol. 56, No. 6, pp. 478-488, 1998, with English abstract.

Tsujiuchi et al., "Novel Microorganism Having Ability to Produce Pyripyropenes", Journal of Technical Disclosure No. 500997/2008, Feb. 13, 2008.

Chinese Office Action issued Jun. 13, 2013 in corresponding Chinese Application No. 201080011214.9 (with English translation).

Office Action issued Feb. 7, 2014 in corresponding Chinese Application No. 201080065119.7, with English translation thereof.

International Search Report issued Mar. 8, 2011 in International (PCT) Application No. PCT/JP2010/070414.

English translation of Egyptian Office Action issued in Egyptian Application No. PCT/NA2012/001483.

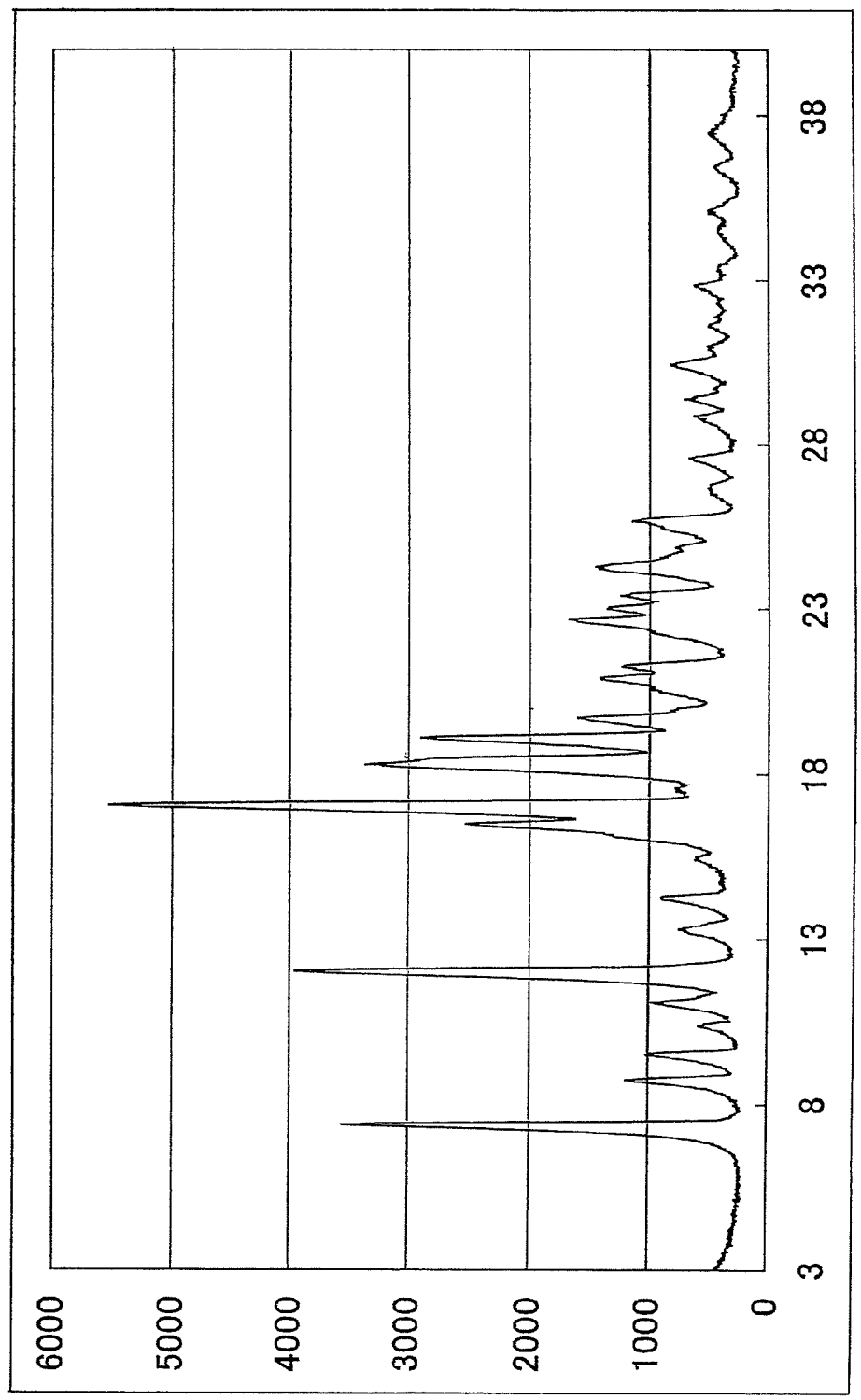

PROCESS FOR PRODUCING PYRIPYROPENE DERIVATIVES

CROSS-REFERENCE OF RELATED APPLICATION

This patent application is an application claiming priority based on prior Japanese Patent Applications, Japanese Patent Application No. 116305/2009 (filing date: May 13, 2009) and Japanese Patent Application No. 44416/2010 (filing date: Mar. 1, 2010). The whole disclosures of the prior applications are incorporated herein by reference.

BACKGROUND OF THE INVENTION

1. Field of Invention

The present invention relates to a process for producing pyripyropene derivatives useful as pest control agents and more specifically relates to a process for producing pyripyropene derivatives that have acyloxy at the 1-position and 11-position and hydroxyl at the 7-position thereof.

2. Background Art

Pyripyropene derivatives having acyloxy at the 1-position and 11-position and hydroxyl at the 7-position thereof are compounds that have control effects against pests, as described in WO 2006/129714.

WO 2006/129714 and Japanese Patent Application Laid-Open No. 259569/1996 disclose a process for producing pyripyropene derivatives having acyloxy at the 1-position and 11-position and hydroxyl at the 7-position thereof. According to the production process, the pyripyropene derivatives are purified or isolated from a plurality of products produced by nonselective hydrolysis of acyloxy using a 1,7,11-triacyloxy compound as a starting compound.

Further, Japanese Patent Application Laid-Open No. 259569/1996 describes the use of a combination of protective groups for the synthesis of pyripyropene derivatives. Journal of Antibiotics Vol. 49, No. 11, p. 1149 (1996), Bioorganic Medicinal Chemistry Letter Vol. 5, No. 22, p. 2683 (1995), and Japanese Patent Application Laid-Open No. 269065/1996 disclose a synthesis example that introduces acyl into the 7-position by utilizing a protective group.

WO 2009/022702 discloses a process for producing 1,11-diacyl-7-deacetylpyripyropene from 1,7,11-trideacetylpyripyropene utilizing a protective group.

Pyripyropene derivatives having acyloxy at the 1-position and 11-position and hydroxyl at the 7-position have hitherto been produced through a plurality of steps using non-selective hydrolysis of a 1,7,11-triacyloxy compound and using a protective group. Accordingly, in the production of pyripyropene derivatives on a commercial scale, a further enhancement in production efficiency, for example, through a reduction in production cost, an improvement in yield, simplification of purification and isolation, or a reduction in number of steps has been desired.

SUMMARY OF THE INVENTION

The present inventors have succeeded in producing a contemplated useful 1,11-diacyloxy compound through a short process by selectively acylating, either directly or stepwise, hydroxyl at the 1-position and 11-position of a trideacyl compound (Japanese Patent Application Laid-Open No. 259569/1996 and Journal of Technical Disclosure No. 500997/2008) easily produced from pyripyropene A (a naturally occurring substance) and its analogue (Pure Appl. Chem., vol. 71, No. 6, pp. 1059-1064, 1999; WO 94/09147; Japanese Patent Application Laid-Open No. 239385/1996, Japanese Patent Application Laid-Open No. 259569/1996, Bioorganic Medicinal Chemistry Letter Vol. 5, No. 22, p. 2683 (1995); and WO 2004/060065), which has led to the completion of the present invention.

1. According to the present invention, there is provided a process for producing compound C represented by formula C:

[Chemical formula 1]

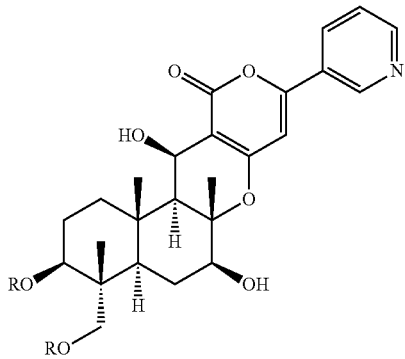

C wherein R represents straight chain, branched chain, or cyclic $C_{2-6}$ alkylcarbonyl, provided that, when the alkyl moiety in the alkylcarbonyl group is of a branched chain or cyclic type, R represents $C_{3-6}$ alkylcarbonyl, the process comprising:

selectively acylating, through one to three steps, hydroxyl groups at the 1-position and 11-position of compound B1 represented by formula B1:

[Chemical formula 2]

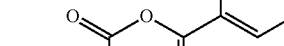

B1 with acylating agent in the presence or absence of a base.

2. According to the present invention, there is provided the process according to the above item 1., characterized in that compound C is acylated from compound B1 through a single step. That is, according to this embodiment, in the process according to the above item 1., compound C is produced by acylating hydroxyl groups at the 1-position and 11-position of compound B1 through a single step.

3. According to the present invention, there is provided the process according to the above item 1., characterized in that the acylation is carried out through two steps consisting of the steps of:

acylating a hydroxyl group at the 11-position of compound B1 with an acylating agent to give compound B2 represented by formula B2:

[Chemical formula 3]

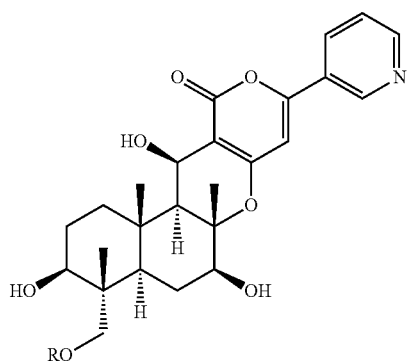

B2 wherein R is as defined in formula C in the above item 1.; and further acylating a hydroxyl group at the 1-position of compound B2. That is, according to this embodiment, in the process according to the above item 1., compound C is produced by acylation through two steps consisting of the steps of: acylating a hydroxyl group at the 11-position of compound B1 with an acylating agent to give compound B2; and further acylating a hydroxyl group at the 1-position of compound B2.

4. According to another aspect of the present invention, there is provided the process according to the above item 1., characterized in that the acylation is carried out through three steps consisting of the steps of: acylating a hydroxyl group at the 11-position of compound B1 to give compound B2; transferring acyl at the 11-position of compound B2 to a hydroxyl at the 1-position to give compound B3 represented by formula B3:

[Chemical formula 4]

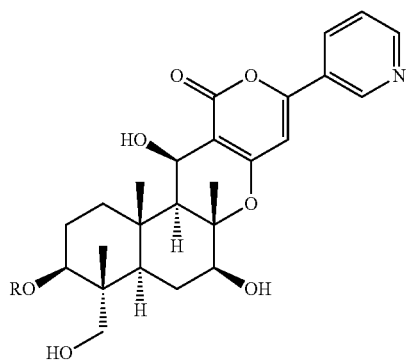

B3 wherein R is as defined in formula C in the above item 1.; and acylating a hydroxyl group at the 11-position of compound B3. That is, according to this embodiment, in the process according to the above item 1., compound C is produced by acylation through three steps consisting of the steps of: acylating a hydroxyl group at the 11-position of compound B1 to give compound B2; transferring acyl at the 11-position of compound B2 to a hydroxyl at the 1-position to give compound B3; and acylating a hydroxyl group at the 11-position of compound B3.

5. Further, according to the present invention, there is provided the process according to any one of the above items 1. to 4., comprising, as a step of producing compound B1, hydrolyzing acyl groups at the 1-position, 7-position, and 11-position of compound A1 represented by formula A1 in the presence of a base:

[Chemical formula 5]

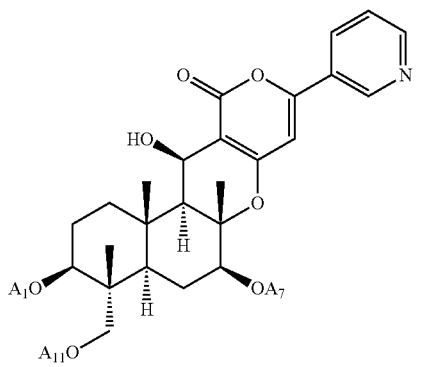

A1 wherein $A_1$, $A_7$, and $A_{11}$, which may be the same or different, represent acetyl or propionyl. That is, according to this embodiment, the process according to the above items 1. to 4. further comprises, as a step of producing compound B1, hydrolyzing acyl groups at the 1-position, 7-position, and 11-position of compound A1 in the presence of a base.

6. According to still another aspect of the present invention, there is provided the process for producing compound C, which comprises the steps of: acylating hydroxyl groups at the 1-position, 11-position, and 7-position of compound B1 to give compound B4 represented by formula B4:

[Chemical formula 6]

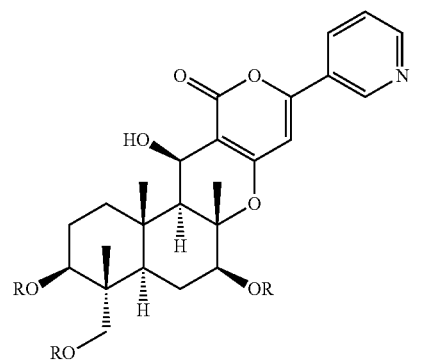

B4 wherein R is as defined above; and then selectively deacylating a hydroxyl group at the 7-position.

According to a further aspect of the present invention, there is provided a method for isolating and purifying solvate crystals of compound C produced by a process according to any one of the above items 1. to 5., the method comprising: adding a proper solvent to a crude product of compound C obtained by concentrating a reaction solution containing compound C produced by any one of the above items 1. to 5. under the reduced pressure; concentrating an ethyl acetate extract of the reaction solution containing compound C produced by the process according to any one of the above items 1. to 5.; or further adding a selected solvent to the concentrate to precipitate solvate crystals of compound C.

According to another aspect of the present invention, there is provided a method for isolating and purifying solvate crystals of compound C, the method comprising the steps of:
(a) extracting a reaction solution containing compound C with an organic solvent selected from the group consisting of methyl acetate, ethyl acetate, butyl acetate, toluene, chlorobenzene, chloroform, dichloromethane, diethyl ether, diisopropyl ether, tetrahydrofuran, and dioxane and concentrating the extract after or without drying;
(b) evaporating the reaction solution containing compound C to dryness to give a crude product and then dissolving the crude product in an organic solvent selected from the group consisting of methyl acetate, ethyl acetate, butyl acetate, toluene, chlorobenzene, chloroform, dichloromethane, diethyl ether, diisopropyl ether, tetrahydrofuran, dioxane, methanol, and ethanol at room temperature or under heating; or
(c) evaporating the reaction solution containing compound C to dryness to give a crude product, dissolving the crude product in an organic solvent selected from the group consisting of methyl acetate, ethyl acetate, butyl acetate, toluene, chlorobenzene, chloroform, dichloromethane, diethyl ether, diisopropyl ether, tetrahydrofuran, dioxane, methanol, and ethanol at room temperature or under heating, and adding a poor solvent selected from the group consisting of heptane, hexane, and cyclohexane to the solution. In a preferred embodiment of the present invention, said step (a) should be a step of (a') extracting a reaction solution containing compound C with ethyl acetate, and concentrating the extract after or without drying. In another preferred embodiment of the present invention, said step (b) should be a step of (b') evaporating the reaction solution containing compound C to dryness to give a crude product and then dissolving the crude product in ethyl acetate at room temperature or under heating. In another preferred embodiment of the present invention, said step (c) should be a step of (c') evaporating the reaction solution containing compound C to dryness to give a crude product, dissolving the crude product in ethyl acetate at room temperature or under heating, and adding hexane to the solution.

According to still another aspect of the present invention, there is provided the process for producing compound C from compound B1 according to any one of the above items 1. to 5., which comprises the step of isolating and purifying compound C by crystallization from a reaction solution containing compound C. That is, according to this embodiment, the process according to any one of above items 1. to 5. further comprises the step of isolating and purifying compound C by crystallization from a reaction solution containing compound C.

According to the present invention, pyripyropene derivatives that have acyloxy at the 1-position and 11-position and hydroxyl at the 7-position and are useful as insect pest control agents can be efficiently produced through a short process.

BRIEF DESCRIPTION OF THE DRAWINGS

FIG. 1 is a powder X-ray pattern measured for ethyl acetate solvate crystals of 1,11-di-O-cyclopropanecarbonyl-1,7,11-trideacetylpyripyropene A.

DETAILED DESCRIPTION OF THE INVENTION

Production Process

The term "alkyl" as used herein as a substituent or a part of a substituent means alkyl that is of a straight chain, branched chain, or cyclic type or a type of a combination thereof unless otherwise specified.

The symbol "$C_{a-b}$" attached to a substituent as used herein means that the number of carbon atoms contained in the substituent as used herein is a to b. Further, "$C_{a-b}$" in "$C_{a-b}$ alkylcarbonyl" means that the number of carbon atoms in the alkyl moiety excluding the carbon atoms in the carbonyl moiety is a to b.

Specific examples of straight chain, branched chain, or cyclic $C_{2-6}$ alkylcarbonyl represented by R, provided that, when the alkyl moiety in the alkylcarbonyl group is of a branched chain or cyclic type, R represents $C_{3-6}$ alkylcarbonyl, include cyclopropanecarbonyl and propionyl.

According to another preferred embodiment of the present invention, in the process according to any one of the above items 1. to 5., the acylation is carried out in the absence of a base.

According to a preferred embodiment of the present invention, in the process according to any one of the above items 1. to 5., the base used in acylating hydroxyl at the 1-position and 11-position of compound B1 is 2,4,6-collidine or 2,6-lutidine.

According to another preferred embodiment of the present invention, in the process according to the above item 2., the acylating agent is used in an amount of 2.0 to 5.0 equivalents based on compound B1.

According to a further preferred embodiment of the present invention, the process according to the above item 3. is characterized in that the solvent used in the step of producing compound B2 is different from the solvent used in the step of further acylating hydroxyl at the 1-position of compound B2.

According to another preferred embodiment of the present invention, the process according to the above item 4. is characterized in that the step of producing compound B3 from compound B2 is carried out in the presence of a base.

According to still another preferred embodiment of the present invention, the process according to the above item 4. is characterized in that the step of producing compound B3 from compound B2 is carried out in the presence of 1,8-diazabicyclo[5.4.0]undeca-7-ene (DBU) as a base.

According to a further preferred embodiment of the present invention, $C_{2-6}$ alkylcarbonyl represented by R is cyclic $C_{3-6}$ alkylcarbonyl, more preferably cyclopropanecarbonyl.

According to a preferred embodiment of the present invention, in the process according to the above item 3., the base is used in the step of producing compound B2 and in the step of further acylating hydroxyl at the 1-position of compound B2, the amount of the base used in the step of producing compound B2 being 1.0 to 3.0 equivalents based on compound B1, the total amount of the base used in the step of producing compound B2 and the base used in the step of further acylating hydroxyl at the 1-position of compound B2 being 2.0 to 4.5 equivalents, more preferably 2.0 to 3.0 equivalents.

According to a preferred embodiment of the present invention, in the process according to any one of the above items 1. to 4., the acylating agent is used in an amount of 2.0 to 5.0 equivalents based on compound B1.

According to a preferred embodiment of the present invention, in the process according to the above item 3., the acylating agent is used in the step of producing compound B2 and in the step of further acylating hydroxyl at the 1-position of compound B2, the amount of the acylating agent used in the step of producing compound B2 being 1.0 to 3.5 equivalents based on compound B1, the total amount of the acylating agent used in the step of producing compound B2 and the acylating agent used in the step of further acylating hydroxyl at the 1-position of compound B2 being 2.0 to 4.5 equivalents.

According to another preferred embodiment of the present invention, there is provided use of compound B2 as an intermediate compound in the production of compound C from compound B1. That is, in the embodiment, use of compound B2 in the production of compound C is provided.

According to still another preferred embodiment of the present invention, there is provided use of compound B2 and compound B3 as an intermediate compound in the production of compound C from compound B1. That is, in this embodiment, use of compound B3 in the production of compound C is provided.

The present invention will be described in more detail according to the following scheme.

[Chemical formula 7]

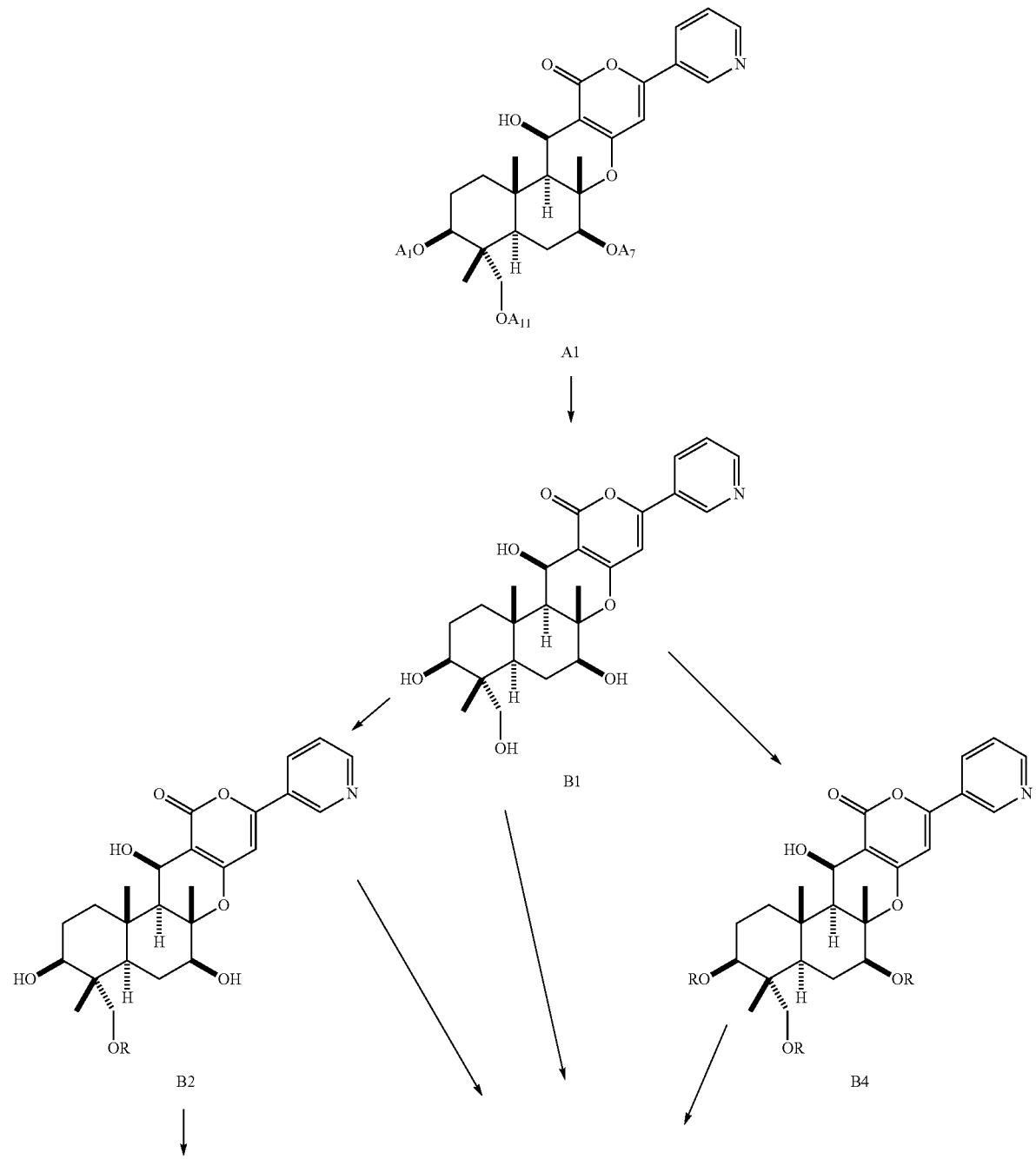

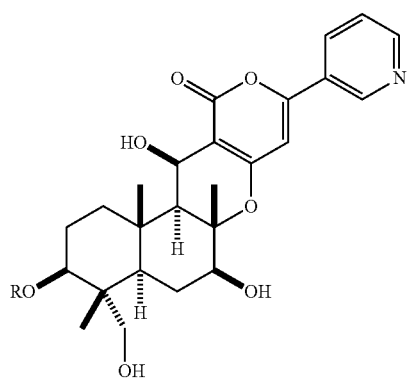

B3

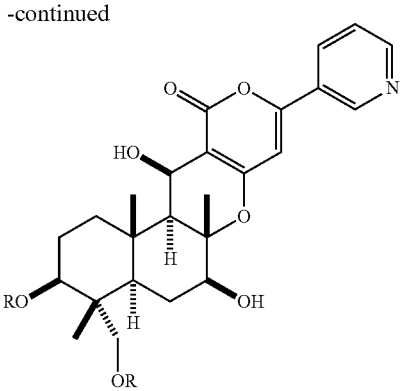

C wherein $A_1$, $A_7$, $A_{11}$, and R are as defined above.

The product produced in each step in the scheme may also be used without post treatment or isolation in the next step.

1-1: Production of Compound B1 from Compound A1

Compound A1 can be produced by a process described, for example, in Pure Appl. Chem., vol. 71, No. 6, pp. 1059-1064, 1999; Japanese Patent Application Laid-Open No. 239385/1996, Japanese Patent Application Laid-Open No. 184158/1994, WO 2004/060065, Japanese Patent Application Laid-Open No. 259569/1996, or Bioorganic Medicinal Chemistry Letter vol. 5, No. 22, p. 2683.

When compound A1 as a starting material is pyripyropene A, pyripyropene A may be one produced by a process described in Journal of Synthetic Organic Chemistry (1998), Vol. 56, No. 6, p. 478-488 or WO 94/09147.

Compound B1 may also be a derivative produced by a process described, for example, in Japanese Patent Application Laid-Open No. 259569/1996 or Journal of Technical Disclosure No. 50997/2008.

A process described in WO 2009/022702 may be mentioned as a process for producing compound B1 from compound A1, and compound B1 may be produced by hydrolyzing acyl at the 1-position, 7-position, and 11-position of compound A1 in the presence of a base.

More specifically, solvents usable herein include alcohol solvents having 1 to 4 carbon atoms such as methanol; ether solvents such as diethyl ether, diisopropyl ether, tetrahydrofuran, and dioxane; aprotic polar organic solvents such as N,N-dimethylformamide, dimethylsulfoxide, N,N-dimethylacetamide, and acetonitrile; halogenated solvents such as dichloromethane and chloroform; or water; and mixed solvents composed of two or more of these solvents.

Bases usable herein include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide; alkali metals such as sodium methoxide, sodium ethoxide, and potassium tert-butoxide; alkoxides of alkaline earth metals; and organic bases such as 1,8-diazabicyclo[5.4.0]undeca-7-ene, 1,5-diazabicyclo[4.3.0]nona-5-ene, triethylamine, diisopropylethylamine, pyridine, hydrazine, and guanidine. Preferred are 1,8-diazabicyclo[5.4.0]undeca-7-ene, 1,5-diazabicyclo[4.3.0]nona-5-ene, sodium carbonate, potassium carbonate, sodium hydrogen carbonate, potassium hydrogen carbonate, sodium hydroxide, and potassium hydroxide.

The amount of the base used is preferably 0.01 to 4.5 equivalents based on the amount of compound A1. The reaction temperature is preferably −20° C. to 50° C. The reaction time is preferably 0.5 hr to 72 hr.

2-1: Production of Compound C from Compound B1

(1) Step of Producing Compound C Directly from Compound B1

Solvents usable in the process for producing compound C from compound B1 in the above item 2. include ether solvents such as diethyl ether, diisopropyl ether, tetrahydrofuran, and dioxane; aprotic polar organic solvents such as N,N-dimethylformamide, dimethylsulfoxide, N,N-dimethylacetamide, acetonitrile, N-methyl-2-pyrrolidinone, N-methyl-2-piperazinone, and N,N-dimethyl-2-imidazolidinone; halogenated solvents such as dichloromethane and chloroform; or aromatic hydrocarbon solvents such as toluene; and mixed solvents composed of two or more of these solvents. Preferred are aprotic polar organic solvents. More preferred are N-methyl-2-pyrrolidinone and N,N-dimethyl-2-imidazolidinone. Particularly preferred is N-methyl-2-pyrrolidinone.

The process according to the above item 2. is preferably carried out in the absence of a base. However, when the process is carried out in the presence of a base, examples of usable bases include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide; and organic bases such as 1,8-diazabicyclo[5.4.0]undeca-7-ene, 1,5-diazabicyclo[4.3.0]nona-5-ene, triethylamine, diisopropylethylamine, pyridine, guanidine, lutidine, collidine, 2,2'-bipyridyl, triphenylamine, quinoline, N,N-dimethylaniline, and N,N-diethylaniline. Preferred are pyridine, 2,6-lutidine, 2,4,6-collidine, 2,2'-bipyridyl, triphenylamine, N,N-dimethylaniline, N,N-diethylaniline and the like. More preferred are 2,6-lutidine, 2,4,6-collidine, triphenylamine, N,N-dimethylaniline, and N,N-diethylaniline. Particularly preferred are 2,6-lutidine and 2,4,6-collidine.

When the base is used, the amount of the base is preferably 2.0 to 4.5 equivalents, more preferably 2.0 to 3.0 equivalents, based on the amount of compound B1.

Group R can be introduced into the 1-position and 11-position using ROH, RCl, $(R)_2O$, or a mixed acid anhydride, preferably RCl or $(R)_2O$, as an acylating agent corresponding to contemplated R. The reaction may be carried out in the presence or absence of a base or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop. Preferably, the reaction is carried out using RCl or (R)$_2$O in the presence or absence of a base.

More preferred acylating agents include cyclopropanecarbonyl chloride, butyryl chloride, and cyclopropanecarboxylic acid anhydride.

The amount of the acylating agent used is preferably 2.0 to 5.0 equivalents, more preferably 2.2 to 4.5 equivalents, based on the amount of compound B1. This amount is used at a time or in two to five divided portions.

The reaction temperature is preferably −20° C. to 50° C., more preferably −10° C. to 50° C., still more preferably −10° C. to room temperature. The reaction time is preferably 0.1 hr to 7 days, more preferably 3 hr to 4 days.

According to this process, compound C can be produced from compound B1 through a single step at a yield of not less than 40%.

(2) Step of Producing Compound B2 from Compound B1

Solvents usable in the process for producing compound B2 from compound B1 in the above item 3. or 4. include ether solvents such as diethyl ether, diisopropyl ether, tetrahydrofuran, and dioxane; aprotic polar organic solvents such as N,N-dimethylformamide, dimethylsulfoxide, N,N-dimethylacetamide, acetonitrile, N-methyl-2-pyrrolidinone, N-methyl-2-piperazinone, and N,N-dimethyl-2-imidazolidinone; halogenated solvents such as dichloromethane and chloroform; or aromatic hydrocarbon solvents such as toluene; and mixed solvents composed of two or more of these solvents. Preferred are aprotic polar organic solvents. Particularly preferred is N-methyl-2-pyrrolidinone.

The reaction may be carried out without use of a base. However, when the base is used, examples of usable bases include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide; and organic bases such as 1,8-diazabicyclo[5.4.0]undeca-7-ene, 1,5-diazabicyclo[4.3.0]nona-5-ene, triethylamine, diisopropylethylamine, pyridine, guanidine, lutidine, collidine, 2,2'-bipyridyl, triphenylamine, quinoline, N,N-dimethylaniline, and N,N-diethylaniline. Preferred are pyridine, 2,6-lutidine, 2,4,6-collidine, 2,2'-bipyridyl, triphenylamine, N,N-dimethylaniline, N,N-diethylaniline and the like. More preferred are triethylamine, 2,6-lutidine, 2,4,6-collidine, triphenylamine, N,N-dimethylaniline, and N,N-diethylaniline. Particularly preferred are triethylamine and 2,6-lutidine.

ROH, RCl, (R)$_2$O, or a mixed acid anhydride, preferably RCl or (R)$_2$O, is used as an acylating agent to be introduced as group R. The reaction may be carried out in the presence or absence of a base or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop. Preferably, the reaction is carried out using RCl or (R)$_2$O in the presence or absence of a base.

More preferred acylating agents include cyclopropanecarbonyl chloride and cyclopropanecarboxylic acid anhydride.

The amount of the acylating agent used is preferably 1.0 to 3.5 equivalents, more preferably 1.1 to 3.0 equivalents, based on the amount of compound B1.

When the base is used, the amount of the base is preferably 1.0 to 3.0 equivalents, more preferably 1.1 to 2.5 equivalents, based on the amount of compound B1.

The reaction temperature is preferably −20° C. to 50° C., more preferably −10° C. to 50° C. The reaction time is preferably 0.1 hr to 7 days, more preferably 45 min to 48 hr.

(3) Step of Producing Compound C from Compound B2

Solvents usable in the process for producing compound C from compound B2 in the above item 3. include ether solvents such as diethyl ether, diisopropyl ether, tetrahydrofuran, and dioxane; aprotic polar organic solvents such as N,N-dimethylformamide, dimethylsulfoxide, N,N-dimethylacetamide, acetonitrile, N-methyl-2-pyrrolidinone, N-methyl-2-piperazinone, and N,N-dimethyl-2-imidazolidinone; halogenated solvents such as dichloromethane and chloroform; or aromatic hydrocarbon solvents such as toluene; and mixed solvents composed of two or more of these solvents. Preferred are aprotic polar organic solvents. Particularly preferred is N-methyl-2-pyrrolidinone.

The reaction may be carried out without use of a base. However, when the base is used, examples of usable bases include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide; and organic bases such as 1,8-diazabicyclo[5.4.0]undeca-7-ene, 1,5-diazabicyclo[4.3.0]nona-5-ene, triethylamine, diisopropylethylamine, pyridine, guanidine, lutidine, collidine, 2,2'-bipyridyl, triphenylamine, quinoline, N,N-dimethylaniline, and N,N-diethylaniline. Preferred are pyridine, 2,6-lutidine, 2,4,6-collidine, 2,2'-bipyridyl, triphenylamine, N,N-dimethylaniline, N,N-diethylaniline and the like. More preferred are triethylamine, 2,6-lutidine, 2,4,6-collidine, triphenylamine, N,N-dimethylaniline, and N,N-diethylaniline. Particularly preferred are triethylamine and 2,6-lutidine.

ROH, RCl, (R)$_2$O, or a mixed acid anhydride, preferably RCl or (R)$_2$O, is used as an acylating agent to be introduced as group R. The reaction may be carried out in the presence or absence of a base or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop. Preferably, the reaction is carried out using RCl or (R)$_2$O in the presence or absence of a base.

More preferred acylating agents include cyclopropanecarbonyl chloride and cyclopropanecarboxylic acid anhydride.

When the base is used, the amount of the base is preferably 0.1 to 5.0 equivalents, more preferably 0.1 to 3.0 equivalents based on the amount of compound B2. In a more preferable embodiment, total amount of the base used in this step and in the step described in the above item (2) is 2.0 to 4.5 equivalents, more preferably 2.0 to 3.0 equivalents.

The amount of the acylating agent used is preferably 1.0 to 3.0 equivalents based on the amount of compound B1, more preferably 2.0 to 4.5 equivalents in terms of total amount of the acylating agent used in this step and in the step described in the above item (2).

The reaction temperature is preferably −20° C. to 60° C. The reaction time is preferably 0.1 hr to 7 days.

This step may also be continuously carried out without taking out the product produced in the step described in the above item (2).

(4) Step of Producing Compound B3 from Compound B2

Solvents usable in the process for producing compound B3 from compound B2 in the above item 4. include ether solvents such as diethyl ether, diisopropyl ether, tetrahydrofuran, and dioxane; aprotic polar organic solvents such as N,N-dimethylformamide, dimethylsulfoxide, N,N-dimethylacetamide, acetonitrile, N-methyl-2-pyrrolidinone, N-methyl-2-piperazinone, and N,N-dimethyl-2-imidazolidinone; halogenated solvents such as dichloromethane and chloroform; or aromatic hydrocarbon solvents such as toluene, chlorobenzene, and dichlorobenzene; and mixed solvents composed of two or more of these solvents. Preferred are aprotic polar organic solvents.

Bases usable herein include inorganic bases such as sodium carbonate, potassium carbonate, sodium hydrogen carbonate, potassium hydrogen carbonate, cesium carbonate, sodium hydroxide, potassium hydroxide, sodium hydride, potassium hydride, sodium cyanide, potassium cyanide, magnesium hydroxide, calcium hydroxide, lithium hydroxide, barium hydroxide, and potassium t-butoxide; and organic bases such as 1,8-diazabicyclo[5.4.0]undeca-7-ene, 1,5-diazabicyclo[4.3.0]nona-5-ene, triethylamine, diisopropylethylamine, pyridine, guanidine, lutidine, collidine, quinoline, N,N-dimethylaniline, N,N-diethylaniline, phosphazene. Preferred are potassium carbonate, cesium carbonate, potassium t-butoxide, 1,8-diazabicyclo[5.4.0]undeca-7-ene, and 1,5-diazabicyclo[4.3.0]nona-5-ene and the like. More Preferred are 1,8-diazabicyclo[5.4.0]undeca-7-ene and 1,5-diazabicyclo[4.3.0]nona-5-ene.

The amount of the base used is preferably 0.1 to 3.0 equivalents, more preferably 0.1 to 2.0 equivalents, based on the amount of compound B2.

The reaction temperature is preferably 0° C. to 150° C. The reaction time is preferably 0.1 hr to 7 days.

(5) Step of Producing Compound C from Compound B3

Solvents usable in the process for producing compound C from compound B3 in the above item 4. include ether solvents such as diethyl ether, diisopropyl ether, tetrahydrofuran, and dioxane; aprotic polar organic solvents such as N,N-dimethylformamide, dimethylsulfoxide, N,N-dimethylacetamide, acetonitrile, N-methyl-2-pyrrolidinone, N-methyl-2-piperazinone, and N,N-dimethyl-2-imidazolidinone; halogenated solvents such as dichloromethane and chloroform; or aromatic hydrocarbon solvents such as toluene; and mixed solvents composed of two or more of these solvents. Preferred are aprotic polar organic solvents. Particularly preferred is N-methyl-2-pyrrolidinone.

The reaction may be carried out without use of a base. However, when the base is used, examples of usable bases include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide; and organic bases such as 1,8-diazabicyclo[5.4.0]undeca-7-ene, 1,5-diazabicyclo[4.3.0]nona-5-ene, triethylamine, diisopropylethylamine, pyridine, guanidine, lutidine, collidine, 2,2'-bipyridyl, triphenylamine, quinoline, N,N-dimethylaniline, and N,N-diethylaniline. Preferred are pyridine, 2,6-lutidine, 2,4,6-collidine, 2,2'-bipyridyl, triphenylamine, N,N-dimethylaniline, N,N-diethylaniline and the like. More preferred are 2,6-lutidine, 2,4,6-collidine, triphenylamine, N,N-dimethylaniline, and N,N-diethylaniline.

ROH, RCl, $(R)_2O$, or a mixed acid anhydride, preferably RCl or $(R)_2O$, is used as an acylating agent to be introduced as group R. The reaction may be carried out in the presence or absence of a base or using a condensing agent such as dicyclohexylcarbodiimide, 1-ethyl-3-(3-dimethylaminopropyl) carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop. Preferably, the reaction is carried out using RCl or $(R)_2O$ in the presence or absence of a base.

More preferred acylating agents include cyclopropanecarbonyl chloride and cyclopropanecarboxylic acid anhydride.

When the base is used, the amount of the base is preferably 1.0 to 3.0 equivalents based on the amount of compound B2.

The amount of the acylating agent used is preferably 1.0 to 2.5 equivalents based on the amount of compound B1.

The reaction temperature is preferably −20° C. to 60° C. The reaction time is preferably 0.1 hr to 7 days.

(6) Method for Purifying and Isolating Compound C from Crude Product

A method for obtaining compound C by crystallization is preferably mentioned as a method for purifying and isolating compound C from a reaction solution or a crude product of compound C produced in the process described in the above item (1), (3), or (5). The crystals may be obtained as solvate crystals comprising a solvent incorporated in a crystal lattice. Alternatively, compound C free from any solvent or water can be obtained by drying the solvate crystals, or by producing precipitates, for example, by dissolving the solvate crystals in methanol and adding water to the solution, collecting the precipitates by filtration, and drying the collected precipitates by heating under the reduced pressure.

According to a preferred embodiment for obtaining crystals of compound C, there is provided the method that comprises extracting a reaction solution containing compound C, obtained by the process according to any one of the above items 1. to 5., with an organic solvent selected from the group consisting of methyl acetate, ethyl acetate, butyl acetate, toluene, chlorobenzene, chloroform, dichloromethane, and ether, concentrating the extract after or without drying and, in this state, allowing crystallization to take place, or the method that comprises evaporating the reaction solution containing compound C to dryness to give a crude product, dissolving the crude product in an organic solvent selected from the group consisting of methyl acetate, ethyl acetate, butyl acetate, toluene, chlorobenzene, chloroform, dichloromethane, ether, methanol, and ethanol at room temperature or under heating, and adding a poor solvent selected from the group consisting of heptane, hexane, and cyclohexane to the solution to cause crystallization. The ether used in the method is preferably selected from diethyl ether, diisopropyl ether, tetrahydrofuran, and dioxane.

A more specific example of the method for obtaining crystals of compound C comprises: either the step of adding a solvent to the reaction solution, removing the solvent by distillation to give a crude product, and adding ethyl acetate to the crude product, or the step of concentrating the ethyl acetate extract of the reaction solution; and isolating ethyl acetate solvate crystals after standing at room temperature or optionally after heating. If necessary, pentane, hexane, or cyclohexane, preferably hexane, is added to the ethyl acetate extract or the concentrate of the ethyl acetate extract to obtain ethyl acetate solvate crystals. Compound C may be obtained by dissolving the ethyl acetate solvate crystals in methanol, adding water to the solution, collecting the resultant precipitates by filtration, and drying the collected precipitates by heating under the reduced pressure.

2-2: Production of Compound C from Compound B1 through Compound B4

The step of producing compound B4 from compound B1 in the process described in the above item 6. may also be carried out in the absence of a solvent. However, when the step is carried out in the presence of a solvent, examples of usable solvents include ketone solvents such as acetone and diethyl ketone; ether solvents such as diethyl ether, diisopropyl ether, and tetrahydrofuran; ester solvents such as ethyl acetate and butyl acetate; aprotic polar organic solvents such as N,N-dimethylformamide, N,N-dimethylacetamide, dimethylsulfoxide, acetonitrile, N-methyl-2-pyrrolidinone, and N-methyl-2-piperazinone; halogenated hydrocarbon solvents such as dichloromethane and chloroform; or aromatic hydrocarbon solvents such as toluene; and mixed solvents composed of two or more of these solvents.

ROH, RCl, $(R)_2O$, or a mixed acid anhydride may be mentioned as an acylating agent to be introduced as group R. The acylating agent is preferably RCl or $(R)_2O$. The reaction may be carried out in the presence or absence of a base or using a condensing agent such as dicyclohexylcarbodiimide, 1-ethyl-3-(3-dimethylaminopropyl)carbodiimide hydrochloride, carbonyldiimidazole, dipyridyl disulfide, diimidazoyl disulfide, 1,3,5-trichlorobenzoyl chloride, 1,3,5-trichlorobenzoyl anhydride, PyBop, or PyBrop.

Bases usable herein include sodium carbonate, potassium carbonate, sodium hydride, potassium tert-butoxide, sodium methoxide, sodium ethoxide, pyridine, lutidine, 4-dimethylaminopyridine, imidazole, 1,8-diazabicyclo[5.4.0]undeca-7-ene, 1,5-diazabicyclo[4.3.0]nona-5-ene, triethylamine, and diisopropylethylamine.

The reaction temperature is preferably −20° C. to 50° C. The reaction time is preferably 0.5 hr to 48 hr.

Solvents usable in the step of producing compound C from compound B4 in the process described in the above item 6. include alcohol solvents having 1 to 4 carbon atoms such as methanol; ether solvents such as diethyl ether, diisopropyl ether, tetrahydrofuran, and dioxane; aprotic polar organic solvents such as N,N-dimethylformamide, dimethylsulfoxide, N,N-dimethylacetamide, acetonitrile, N-methyl-2-pyrrolidinone, and N-methyl-2-piperazinone; halogenated solvents such as dichloromethane and chloroform; or water; and mixed solvents composed of two or more of these solvents.

Bases usable herein include inorganic bases such as sodium carbonate, potassium carbonate, sodium hydrogen carbonate, potassium hydrogen carbonate, sodium hydroxide, potassium hydroxide, sodium hydride, potassium hydride, sodium cyanide, potassium cyanide, magnesium hydroxide, calcium hydroxide, lithium hydroxide, and barium hydroxide; alkali metals such as sodium methoxide, sodium ethoxide, and potassium tert-butoxide; alkoxides of alkaline earth metals; and organic bases such as 1,8-diazabicyclo[5.4.0]undeca-7-ene, 1,5-diazabicyclo[4.3.0]nona-5-ene, triethylamine, diisopropylethylamine, pyridine, hydrazine, and guanidine. Preferred are 1,8-diazabicyclo[5.4.0]undeca-7-ene, 1,5-diazabicyclo[4.3.0]nona-5-ene, sodium carbonate, potassium carbonate, sodium hydrogen carbonate, potassium hydrogen carbonate, sodium hydroxide, and potassium hydroxide.

The amount of the base used is preferably 0.01 to 24 equivalents based on the amount of compound B4. The reaction temperature is preferably −20° C. to 50° C. The reaction time is preferably 0.5 hr to 14 days.

EXAMPLES

The present invention is further illustrated by the following Examples that are not intended as a limitation of the invention.

The purity described in Experiment Examples means the percentage area of a contemplated substance measured under the following HPLC conditions unless otherwise specified.

Measuring Conditions for HPLC

Column: Inertsil ODS-2 or ODS-4 (5 μm); 4.6φ×150 mm (ODS-2 was used in Examples 1 to 13, and ODS-4 was used in Examples 14 to 20.)
Column temp.: 30° C.
Mobile phase: Water-acetonitrile
Conditions for mobile phase: As shown in Table 1 below

TABLE 1

| | Time (min.) | | | | | | |
|---|---|---|---|---|---|---|---|
| | 0 | 1 | 9 | 17 | 20 | 21.01 | 30 |
| Water (%) | 80 | 80 | 40 | 10 | 10 | 80 | 80 |
| Acetonitrile (%) | 20 | 20 | 60 | 90 | 90 | 20 | 20 |

Flow rate: 1.0 mL/min
Detection wavelength: UV 320 nm

Example 1

Synthesis of 11-O-cyclopropanecarbonyl-1,7,11-trideacetylpyripyropene A 1,7,11-Trideacetylpyripyropene A (1.00 g) synthesized according to the method described in WO2006/129714 was suspended in 5 ml of N-methyl-2-pyrrolidinone, 0.55 ml (2.2 equivalents) of 2,6-lutidine was added to the suspension, and 0.44 ml (2.2 equivalents) of cyclopropanecarbonyl chloride was added dropwise to the suspension at room temperature. After one hr of the dropwise addition, the reaction solution was added dropwise to 200 ml of water. The mixture was stirred for 5 hr, and the resultant precipitate was then collected by filtration, was washed with water, and was dried to give 0.816 g of a powder composed mainly of 11-O-cyclopropanecarbonyl-1,7,11-trideacetylpyripyropene A. Separately, 25 g of sodium chloride was added to the filtrate, and the mixture was extracted with 20 ml of ethyl acetate. The ethyl acetate layer was washed with water, ethyl acetate was removed by distillation, and the residue was dried to give 0.27 g of a foamy material composed mainly of 11-O-cyclopropanecarbonyl-1,7,11-trideacetylpyripyropene A. The powder and the foamy material were combined together, followed by chromatography on silica gel (100 ml of silica gel C-60 manufactured by Merck Ltd.; ethyl acetate-methanol (50:1 (v/v); flow rate 10 ml/min) to give 532 mg of 11-O-cyclopropanecarbonyl-1,7,11-trideacetylpyripyropene A (yield: 46.3%) (purity: 95.6%).

FAB-MS; m/z 526 (M+H)$^+$; $^1$H-NMR (CDCl$_3$) δ 2.15 (1H, dt, J=3.4, 9.5 Hz), 2.42 (1H, bs), 2.96 (1H, s), 3.41 (1H, dd, J=5.1, 11.0 Hz), 3.75 (1H, d, J=11.9 Hz), 3.83 (1H, dd, J=4.9, 11.9 Hz), 4.29 (1H, d, J=11.7 Hz), 5.00 (1H, d, J=3.2 Hz), 6.52 (1H, s), 7.42 (1H, dd, J=4.9, 8.1 Hz), 8.11 (1H, dt, J=2.0, 8.3 Hz), 8.69 (1H, dd, J=1.3, 4.8 Hz), 9.00 (1H, d, J=1.7 Hz)

Example 2

Synthesis of 11-O-cyclopropanecarbonyl-1,7,11-trideacetylpyripyropene A 1,7,11-Trideacetylpyripyropene A (1.00 g) was suspended in 5 ml of N-methyl-2-pyrrolidinone, 0.50 ml (2.0 equivalents) of 2,6-lutidine was added to the suspension, and 0.33 ml (1.7 equivalents) of cyclopropanecarbonyl chloride was added dropwise to the suspension at room temperature. After 45 min of the dropwise addition, the reaction solution was added dropwise to 100 ml of water. Sodium chloride (5 g) was added thereto, and the mixture was stirred overnight. The resultant precipitate was then collected by filtration, was washed with water, and was dried to give 1.053 g of a powder composed mainly of 11-O-cyclopropanecarbonyl-1,7,11-trideacetylpyripyropene A. The powder (526 mg; half amount) was purified by chromatography on silica gel (100 ml of silica gel C-60N (40-50 μm) manufactured by KANTO CHEMICAL CO., INC.; ethyl acetate-methanol (50:1 (v/v); flow rate 5 ml/min) to give 366 mg of 11-O-cyclopropanecarbonyl-1,7,11-trideacetylpyripyropene A (yield: 63.7%) (purity: 95.1%).

Example 3

Synthesis of 1,11-di-O-cyclopropanecarbonyl-1,7,11-trideacetylpyripyropene A 1,7,11-Trideacetylpyripyropene A (1.00 g) was suspended in 5 ml of N-methyl-2-pyrrolidinone, 0.76 ml (2.6 equivalents) of 2,4,6-collidine was added to the suspension, and the mixture was added dropwise to 0.50 ml (2.5 equivalents) of cyclopropanecarbonyl chloride at room temperature. A reaction was allowed to proceed for 8.5 hr. The reaction solution was then added dropwise to 200 ml of water. The mixture was stirred overnight, and the resultant precipitate was then collected by filtration and was dried to give 1.135 g of a powder composed mainly of 1,11-di-O-cyclopropanecarbonyl-1,7,11-trideacetylpyripyropene A. Separately, 25 g of sodium chloride was added to filtrate, and the mixture was extracted with 20 ml of ethyl acetate. The ethyl acetate layer was washed with water, ethyl acetate was removed by distillation, and the residue was dried to give 0.12 g of a foamy material composed mainly of 1,11-di-O-cyclopropanecarbonyl-1,7,11-trideacetylpyripyropene A. The powder and the foamy material were combined together, followed by chromatography on silica gel (150 ml of silica gel C-60 manufactured by Merck Ltd.; only ethyl acetate; flow rate 10 ml/min) to give 743 mg of 1,11-di-O-cyclopropanecarbonyl-1,7,11-trideacetylpyripyropene A (yield: 57.2%) (purity: 80.8%). For the compound thus obtained, FAB-MS and $^1$H-NMR are measured, and, as a result, it was found that the data were in agreement with the data of compound 261 described in WO2006/129714.

FAB-MS; m/z 594 (M+H)$^+$; $^1$H-NMR (CDCl$_3$) δ 3.75 (1H, d, J=12.0 Hz), 3.79 (1H, dd, J=4.6, 11.7 Hz), 3.87 (1H, d, J=11.7 Hz), 4.82 (1H, dd, J=4.9, 11.2 Hz), 4.99 (1H, s), 6.52 (1H, s), 7.42 (1H, dd, J=4.8, 7.9 Hz), 8.10 (1H, d, J=7.8 Hz), 8.69 (1H, d, J=3.9 Hz), 9.00 (1H, s)

Example 4

Synthesis of 1,11-di-O-cyclopropanecarbonyl-1,7,11-trideacetylpyripyropene A 1,7,11-Trideacetylpyripyropene A (1.00 g) was suspended in 4 ml of N-methyl-2-pyrrolidinone, 0.75 ml (3.0 equivalents) of 2,6-lutidine was added to the suspension, and 0.54 ml (2.7 equivalents) of cyclopropanecarbonyl chloride was added dropwise to the suspension at room temperature. A reaction was allowed to proceed for three hr. The reaction solution was added dropwise to 100 ml of water. The mixture was stirred for two hr, and 10 g of sodium chloride was then added thereto. The mixture was then stirred overnight, and the resultant precipitate was collected by filtration, was washed with water, and was dried to give 1.276 g of a powder composed mainly of 1,11-di-O-cyclopropanecarbonyl-1,7,11-trideacetylpyripyropene A. The 1,11-di-O-cyclopropanecarbonyl-1,7,11-trideacetylpyripyropene A thus obtained was purified by chromatography on silica gel (silica gel C-60 manufactured by Merck Ltd.; 50 ml for the first time, 150 ml in collected main fractions for the second time, and only ethyl acetate; flow rate 5 ml/min) to give 576 mg of 1,11-di-O-cyclopropanecarbonyl-1,7,11-trideacetylpyripyropene A (yield: 44.4%) (purity: 88.6%) and 115 mg (yield: 8.8%) (purity: 74.9%).

Example 5

Synthesis of 1,11-di-O-cyclopropanecarbonyl-1,7,11-trideacetylpyripyropene A 1,7,11-Trideacetylpyripyropene A (500 mg) was suspended in 2.5 ml of N-methyl-2-pyrrolidinone, and 0.25 ml (2.5 equivalents) of cyclopropanecarbonyl chloride was added dropwise to the suspension at room temperature. A reaction was allowed to proceed for 24 hr. The reaction solution was added dropwise to 50 ml of water. The mixture was adjusted to pH 7.5 by the addition of 8% sodium bicarbonate water. Sodium chloride (5 g) was then added thereto, and the mixture was stirred overnight. The resultant precipitate was then collected by filtration and was washed with water to give a powder. The powder was dried to give 604 mg of a powder composed mainly of 1,11-di-O-cyclopropanecarbonyl-1,7,11-trideacetylpyripyropene A. The 1,11-di-O-cyclopropanecarbonyl-1,7,11-trideacetylpyripyropene A thus obtained was purified by chromatography on silica gel (100 ml of silica gel C-60N manufactured by KANTO CHEMICAL CO., INC.; only ethyl acetate; flow rate 5 ml/min) to give 338 mg of 1,11-di-O-cyclopropanecarbonyl-1,7,11-trideacetylpyripyropene A (yield: 52.0%) (purity: 93.2%).

Example 6

Synthesis of 1,11-di-O-cyclopropanecarbonyl-1,7,11-trideacetylpyripyropene A 1,7,11-Trideacetylpyripyropene A (500 mg) was suspended in 2.5 ml of N-methyl-2-pyrrolidinone, the suspension was cooled to 0° C., and 0.15 ml (1.5 equivalents) of cyclopropanecarbonyl chloride was added dropwise thereto. The mixture was stirred at 0° C. for 20 hr, and 0.1 ml (1.0 equivalent) of cyclopropanecarbonyl chloride was then additionally added. The mixture was stirred for 66 hr, and 0.1 ml (1.0 equivalent) of cyclopropanecarbonyl chloride was further additionally added. The mixture was stirred for 95 hr and was added dropwise to 50 ml of ice water. The mixture was adjusted to pH 7.5 by the addition of 8% sodium bicarbonate water. Sodium chloride (5 g) was then added thereto, and the mixture was stirred. The resultant precipitate was then collected by filtration and was washed with water. The filtrate was extracted with ethyl acetate, and the ethyl acetate layer was then washed with saturated brine and was dried over anhydrous magnesium sulfate. The solvent was then removed by distillation under the reduced pressure. The residue and the precipitate were combined together, followed by purification by chromatography on silica gel (150 ml of silica gel C-60N manufactured by KANTO CHEMICAL CO., INC.; only ethyl acetate; flow rate 5 ml/min) to give 396 mg of 1,11-di- O-cyclopropanecarbonyl-1,7,11-trideacetylpyripyropene A (yield: 60.9%) (purity: 95.3%).

Example 7

Synthesis of 1,11-di-O-cyclopropanecarbonyl-1,7, 11-trideacetylpyripyropene A

11-O-cyclopropanecarbonyl-1,7,11-trideacetylpyripyropene A (200 mg, purity: 95.6%) obtained in Example 1 was suspended in 1.0 ml of N-methyl-2-pyrrolidinone, and 0.06 ml (1.5 equivalents) of cyclopropanecarbonyl chloride was added dropwise to the suspension at room temperature. A reaction was allowed to proceed for 21.5 hr, and 20 ml of water was added to the reaction solution. The mixture was adjusted to pH 7.5 by the addition of 8% sodium bicarbonate water, and 10 ml of ethyl acetate and 3 g of sodium chloride were added thereto. The mixture was extracted and was then washed with water. Ethyl acetate (10 ml) was further added to the aqueous layer, and the mixture was extracted. The extract was then washed with water and was combined with the ethyl acetate layer obtained above. Ethyl acetate was removed by distillation under the reduced pressure to give a powder (295 mg) composed mainly of 1,11-di-O-cyclopropanecarbonyl-1,7,11-trideacetylpyripyropene A. The powder was purified by chromatography on silica gel (100 ml of silica gel C-60N manufactured by KANTO CHEMICAL CO., INC.; only ethyl acetate; flow rate 5 ml/min) to give 119 mg of 1,11-di-O-cyclopropanecarbonyl-1,7,11-trideacetylpyripyropene A (yield: 55.0%) (purity: 96.5%).

Example 8

Synthesis of 1,7,11-tri-O-cyclopropanecarbonyl-1,7, 11-trideacetylpyripyropene A 1,7,11-Trideacetylpyripyropene A (500 mg) was suspended in 2.5 ml of N-methyl-2-pyrrolidinone, 0.44 ml (5 eq) of pyridine was added to the suspension, and 0.45 ml (4.5 eq) of cyclopropanecarbonyl chloride was added dropwise to the suspension at room temperature. A reaction was allowed to proceed for 1.5 hr. The reaction solution was added dropwise to 50 ml of water. The mixture was stirred for three hr, and 5 g of sodium chloride was then added thereto. Thereafter, the reaction solution was stirred for 1.5 hr, and the resultant precipitate was then collected by filtration and was washed with water. The powder thus obtained was dried to give 721 mg of 1,7,11-tri-O-cyclopropanecarbonyl-1,7,11-trideacetylpyripyropene A as a powder (yield: 99.4%) (purity: 89.6%). For the compound thus obtained, FAB-MS and $^1$H-NMR were measured, and, as a result, it was found that the data were in agreement with compound 218 described in WO 2006/129714.

FAB-MS; m/z 662 (M+H)$^+$; $^1$H-NMR (CDCl$_3$) δ 2.89 (1H, s), 3.72 (1H, d, J=11.7 Hz), 3.82 (1H, d, J=11.7 Hz), 4.79 (1H, dd, J=4.9, 11.5 Hz), 5.01 (1H, bs), 5.02 (1H, dd, J=4.9, 11.2 Hz), 6.46 (1H, s), 7.41 (1H, dd, J=4.8, 7.9 Hz), 8.10 (1H, dt, J=1.7, 6.4 Hz), 8.69 (1H, bs), 9.02 (1H, s)

Example 9

Synthesis of 1,11-O-dicyclopropanecarbonyl-1,7,11-trideacetylpyripyropene A 1,7,11-O-tricyclopropanecarbonyl-1,7,11-trideacetylpyripyropene A (1.0 g) synthesized in Example 8 was dissolved in a 95% aqueous methanol solution (30 mL), and potassium tert-butoxide (85 mg) was added thereto at room temperature. The mixture was stirred at that temperature for 16 hr, and acetic acid was then added thereto. Methanol was removed by distillation under the reduced pressure, and the residue was extracted with chloroform. The chloroform layer was washed with saturated brine and was dried over anhydrous magnesium sulfate. The solvent was then removed by distillation under the reduced pressure to give a crude product of 1,11-O-dicyclopropanecarbonyl-1,7,11-trideacetylpyripyropene A (724 mg, purity: 50%). The crude product was purified by column chromatography on silica gel (Merck silica gel 60F$_{254}$ 0.5 mm; hexane:acetone=10:5.5) to give 1,11-O-dicyclopropanecarbonyl-1,7,11-trideacetylpyripyropene A (370 mg, yield: 41%).

Example 10

Synthesis of 1,11-O-dicyclopropanecarbonyl-1,7,11-trideacetylpyripyropene A (Method Utilizing Crystallization)

1,7,11-O-tricyclopropanecarbonyl-1,7,11-trideacetylpyripyropene A (4 g) synthesized in Example 8 was dissolved by heating in methanol (100 mL), and potassium carbonate (420 mg) was added thereto at room temperature. The mixture was stirred at that temperature for 6 hr, acetic acid (370 mg) and water (100 mL) were added thereto, and the mixture was allowed to stand for 23 hr. The precipitated starting material was removed by filtration, water (50 mL) was then added, and the mixture was allowed to stand for 20 hr. Methanol was removed by distillation under the reduced pressure, and the residue was allowed to stand for 7 hr. As a result, 1,11-O-dicyclopropanecarbonyl-1,7,11-trideacetylpyripyropene A was precipitated, and the precipitated 1,11-O-dicyclopropanecarbonyl-1,7,11-trideacetylpyripyropene A was collected by filtration (900 mg, yield: 25.1%, purity: 81%).

Example 11

Synthesis of 11-O-cyclopropanecarbonyl-1,7,11-trideacetylpyripyropene A 1,7,11-Trideacetylpyripyropene A (4.53 g) was suspended in 22.5 g of N-methyl-2-pyrrolidinone, 1.51 g (1.51 equivalents) of triethylamine and 2.25 g (1.47 equivalents) of cyclopropanecarboxylic acid anhydride were added to the suspension, and the mixture was heated with stirring at 60° C. for 23 hr. Thereafter, the heated mixture was concentrated under the reduced pressure at a bath temperature of 70° C. Water (10 ml) was added to the oil thus obtained for solidification. The solid was washed thrice with 10 ml of water and was collected by filtration. The powder thus obtained was washed with 5 ml of water and was dried under the reduced pressure at 40° C. for one day to give 11-O-cyclopropanecarbonyl-1,7,11-trideacetylpyripyropene A (4.73 g, yield: 91.4%, purity: 76.2%).

Example 12

Synthesis of 1-O-cyclopropanecarbonyl-1,7,11-trideacetylpyripyropene A

11-O-cyclopropanecarbonyl-1,7,11-trideacetylpyripyropene A (199.7 mg, purity: 95.6%) produced in the same manner as in Example 1 was suspended in 2.0 ml of chlorobenzene. DBU (0.02 ml, about 0.4 equivalent) was added to the suspension, and the mixture was heated with stirring at 80° C. for 9 hr. Thereafter, the reaction solution was gradually cooled to room temperature and was stirred at room temperature for two days. Ethyl acetate (20 ml) and 5 ml of water were added thereto, and the organic layer was separated and was concentrated under the reduced pressure. Crystals were precipitated in such a state that chlorobenzene remained in the system. Accordingly, the crystals were collected by filtration and were washed with toluene. The crystals were dried under the reduced pressure at 60° C. overnight to give 1-O-cyclopropanecarbonyl-1,7,11-trideacetylpyripyropene A (153.4 mg, yield: 76.8%, purity: 94.5%).

Example 13

Synthesis of 1,11-di-O-cyclopropanecarbonyl-1,7,11-trideacetylpyripyropene A

1-O-cyclopropanecarbonyl-1,7,11-trideacetylpyripyropene A (500 mg) was suspended in 3.0 ml of N-methyl-2-pyrrolidinone, and the suspension was added dropwise to 0.10 ml (1.0 equivalent) of cyclopropanecarbonyl chloride at 0° C. A reaction was allowed to proceed for one day, and 0.025 ml (0.25 equivalent) of cyclopropanecarbonyl chloride was added thereto. Further, after 41 hr from the addition of cyclopropanecarbonyl chloride, 1.0 ml of N-methyl-2-pyrrolidinone and 0.025 ml (0.25 equivalent) of cyclopropanecarbonyl chloride were added to the reaction solution, and a reaction was allowed to proceed for 65 hr. The reaction solution was then poured into 30 ml of ice water and 50 ml of ethyl acetate. The mixture was neutralized with 8% sodium bicarbonate water, 3 g of sodium chloride was added thereto, and the mixture was stirred, followed by separation. The organic layer was washed twice with 10 ml of water, and the solvent was removed by distillation under the reduced pressure. The powder (678 mg) thus obtained was subjected to chromatography on silica gel (silica gel C-60 (80 ml) manufactured by Merck Ltd.; ethyl acetate-methanol (50:1 (v/v)) to recover 1,11-di-O-cyclopropanecarbonyl-1,7,11-trideacetylpyripyropene A (479 mg, yield: 83.3%, purity: 95.2%) and 51 mg (10.2%) of 1-O-cyclopropanecarbonyl-1,7,11-trideacetylpyripyropene A.

Example 14

Synthesis of 1,11-di-O-cyclopropanecarbonyl-1,7,11-trideacetylpyripyropene A 1,7,11-Trideacetylpyripyropene A (1.00 g) was suspended in 7.0 ml of N-methyl-2-pyrrolidinone, the suspension was cooled to 0° C., and 0.4 ml (2.0 equivalents) of cyclopropanecarbonyl chloride was added dropwise to the suspension.

Thereafter, 0.1 ml (0.5 equivalent) of cyclopropanecarbonyl chloride was additionally added dropwise thereto at 0° C. after the elapse of each of 7 hr, 23 hr, and 26 hr from the completion of the dropwise addition. After 4 days of the dropwise addition, the reaction solution was poured into 50 ml of ethyl acetate and 50 ml of ice water. Further, the mixture was neutralized with 0.7 g of sodium bicarbonate and 8% sodium bicarbonate water, and 5.0 g of sodium chloride was added thereto. The mixture was stirred and was allowed to stand, followed by separation. The organic layer was washed twice with 20 ml of water and was concentrated under the reduced pressure. Ethyl acetate (8.0 ml) was added to the foamy powder thus obtained, the mixture was heated to 60° C., and 8.0 ml of n-hexane was added thereto. The mixture was cooled to 50° C., and a very small amount of a seed crystal was added. After the precipitation of crystals, 2.0 ml of n-hexane was added, and the mixture was stirred overnight. The crystals were collected by filtration, and the collected crystals were washed with 10 ml of n-hexane-ethyl acetate (1:1 (v/v)). The crystals thus obtained were dried overnight at 60° C. to give 1,11-di-O-cyclopropanecarbonyl-1,7,11-trideacetylpyripyropene A (787 mg, yield: 60.5%, purity: 87.5%).

Example 15

Synthesis of 1,11-di-O-cyclopropanecarbonyl-1,7,11-trideacetylpyripyropene A 1,7,11-Trideacetylpyripyropene A (10.0 g) was suspended in 40.0 ml of N-methyl-2-pyrrolidinone, the suspension was cooled to 0° C., and 3.0 ml (1.5 equivalents) of cyclopropanecarbonyl chloride was added dropwise to the suspension.

Thereafter, cyclopropanecarbonyl chloride was additionally added dropwise thereto at 0° C. after the elapse of each of 6 hr (2.0 ml, 1.0 equivalent), 24 hr (1.0 ml, 0.5 equivalent), 32 hr (0.50 ml, 0.25 equivalent), and 48 hr (1.0 ml, 0.5 equivalent) from the completion of the dropwise addition. In addition, N-methyl-2-pyrrolidinone was added after the elapse of 6 hr (20.0 ml) and 48 hr (10.0 ml) from the completion of the dropwise addition. After 96 hr of the dropwise addition, the reaction solution was poured into 100 ml of ethyl acetate and 200 ml of ice water and was stirred, followed by separation.

Ethyl acetate (170 ml) was added to the aqueous layer, the mixture was further neutralized with 10.1 g of sodium bicarbonate, and 20.0 g of sodium chloride was added thereto. The mixture was stirred and was allowed to stand, followed by separation. The organic layer was washed once with 50 ml of 5% brine and twice with 30 ml of water and was concentrated under the reduced pressure. Ethyl acetate was added to the residue to a total volume of 110 ml. The mixture was then heated to 60° C., and 100.0 ml of n-hexane was added thereto. The mixture was cooled to 50° C., and a very small amount of a seed crystal was added. After three hr the precipitation of crystals, 20 ml of n-hexane was added, and the mixture was stirred for two days. The crystals were collected by filtration, and the collected crystals were washed with 50 ml of n-hexane-ethyl acetate (1:1 (v/v)). The crystals thus obtained were dried at 60° C. for one day to give 1,11-di-O-cyclopropanecarbonyl-1,7,11-trideacetylpyripyropene A (8.83 g, weight yield: 67.9%, purity: 86.4%).

Thereafter, a 8.70 g portion in 8.83 g of the 1,11-di-O-cyclopropanecarbonyl-1,7,11-trideacetylpyripyropene A was dissolved in 43.5 ml of methanol, and 29.0 ml of water was added thereto at room temperature. As a result, the solution became milky and hence was heated to 30° C. Methanol (1.0 ml) was added thereto, and a very small amount of a seed crystal was added. After the precipitation of crystals, a mixed solution composed of 15.0 ml of water and 3.0 ml of methanol were added in two divided portions. The mixture was stirred at room temperature overnight and was filtered. The crystals were washed with a mixed solution composed of 16.0 ml of water and 4.0 ml of methanol. The crystals were dried at 80° C. under the reduced pressure to give 1,11-di-O-cyclopropanecarbonyl-1,7,11-trideacetylpyripyropene A (6.22 g, weight yield in total: 48.5%, purity: 94.5%).

Example 16

Synthesis of 1,11-di-O-cyclopropanecarbonyl-1,7,11-trideacetylpyripyropene A 1,7,11-Trideacetylpyripyropene A (10.0 g) was suspended in 40.0 ml of N-methyl-2-pyrrolidinone, the suspension was cooled to 0° C., and 7.0 ml (3.5 equivalents) of cyclopropanecarbonyl chloride was added dropwise to the suspension.

Thereafter, a reaction was allowed to proceed at 0° C. for 53 hr, and the reaction solution was poured into 50 ml of ethyl acetate and 80 ml of ice water. The mixture was stirred at 7° C. or below, followed by separation. Ethyl acetate (30 ml) was added to the aqueous layer, and the mixture was stirred, followed by separation. Ethyl acetate (100 ml) was added to the aqueous layer thus obtained, and the mixture was neutralized with 72 ml of 1N sodium hydroxide and a small amount of 8% sodium bicarbonate water. Sodium chloride (15.0 g) was added to the mixture at 10 to 15° C., and the mixture was stirred and was allowed to stand, followed by separation. The organic layer was washed once with 30 ml of 5% brine and twice with 30 ml of water, and the mixture was concentrated under reduced pressure. Ethyl acetate (20 ml) was added to the residue, the mixture was heated to 60° C., and 14 ml of n-hexane was added thereto. As a result, the solution became milky, and, hence, 4.0 ml of ethyl acetate was added for dissolution. The solution was then cooled to 50° C., and a very small amount of a seed crystal was added. After the elapse of 1.5 hr from the precipitation of crystals, 10 ml of n-hexane was added, and the mixture was stirred overnight. The crystals were collected by filtration and were washed with 30 ml of n-hexane-ethyl acetate (1:1 (v/v)). The crystals were dried at 80° C. for two days to give 1,11-di-O-cyclopropanecarbonyl-1,7,11-trideacetylpyripyropene A (8.48 g, weight yield: 65.2%, purity: 83.4%).

The ethyl acetate solution obtained in the post treatment was neutralized, was washed with brine and water, and was dried under the reduced pressure. Separately, the filtrate obtained in the collection of the crystals and the washings were concentrated and dried. These two materials thus obtained were combined together (5.71 g), and the mixture was dissolved in methanol (30.0 ml). Thereafter, 5.16 ml of a 5 N sodium hydroxide solution was added dropwise at room temperature. A 5 N sodium hydroxide solution (2.0 ml) was further added dropwise after the elapse of 1.5 hr from the dropwise addition of the 5 N sodium hydroxide solution. The mixture was stirred at room temperature for 18 hr, was filtered, and was washed with 22 ml of methanol-water (1:1 (v/v)). The crystals thus obtained were dried at 80° C. for one day to obtain the starting material, i.e., 1,7,11-trideacetylpyripyropene A (1.96 g, recovery: 19.6%, purity: 94.5%).

When the recovery was taken into consideration, the yield of 1,11-di-O-cyclopropanecarbonyl-1,7,11-trideacetylpyripyropene A was 81.0%.

Example 17

Synthesis of 1,11-di-O-cyclopropanecarbonyl-1,7,11-trideacetylpyripyropene A 1,7,11-Trideacetylpyripyropene A (10.0 g) was suspended in 40.0 ml of N-methyl-2-pyrrolidinone, the suspension was cooled to 3° C., and 7.0 ml (3.5 equivalents) of cyclopropanecarbonyl chloride was added dropwise to the suspension. A reaction was then allowed to proceed at 0° C. for 48 hr, and the reaction solution was poured into 50 ml of ethyl acetate and 80 ml of ice water. The mixture was stirred at 10° C. or below, followed by separation. Ethyl acetate (100 ml) was added to the aqueous layer, the mixture was neutralized with 25 ml of 5 N sodium hydroxide and a small amount of 8% sodium bicarbonate water, and 8 g of sodium chloride was added thereto at 10 to 15° C. The mixture was stirred for dissolution and was allowed to stand, followed by separation. The organic layer was washed once with 30 ml of 5% brine and twice with 30 ml of water, was concentrated to 40 ml under the reduced pressure, and was stirred at room temperature for 5 hr to precipitate crystals. Thereafter, 20 ml of n-hexane was added over a period of two hr, and the mixture was stirred overnight. The crystals were filtered and were washed with 30 ml of n-hexane-ethyl acetate (1:1 (v/v)). The crystals were dried at room temperature under the reduced pressure for 30 min to give 7.31 g of crystals of 1,11-di-O-cyclopropanecarbonyl-1,7,11-trideacetylpyripyropene A. An NMR spectrum (apparatus: Lambda-400, solvent: CDCl$_3$, the ratio between the integral value of two protons of CH$_3$COOC$\underline{H}_2$CH$_3$ at δ 4.12 and the integral value of one proton of 1,11-di-O-cyclopropanecarbonyl-1,7,11-trideacetylpyripyropene A) of the crystals thus obtained showed that the content of ethyl acetate was 0.96 mol based on 1.0 mol of 1,11-di-O-cyclopropanecarbonyl-1,7,11-trideacetylpyripyropene A (weight yield (as ethyl acetate solvate): 49.1%, purity: 88.9%).

The powder X-ray diffraction pattern of the crystals had the following values.

Powder X-Ray Diffraction Pattern

Apparatus: RINT 2200 (manufactured by Rigaku Denki Co., Ltd.)

Measuring conditions: X ray: CuKα/40 kV/20 mA, sampling width: 0.020°, scan speed: 0.500°/min, scanning width: 2θ/θ, and scanning range: 3.0 to 40.0°

Characteristic peaks appeared at the following diffraction angles [2θ(°)].

Diffraction angles (2θ): 7.4±0.1°, 12.0±0.1°, 17.0±0.1°, 18.3±0.1°, and 19.1±0.1°

A powder X-ray diffraction pattern is shown in FIG. 1.

Example 18

Synthesis of 1,11-di-O-cyclopropanecarbonyl-1,7,11-trideacetylpyripyropene A 1,7,11-Trideacetylpyripyropene A (10.0 g) was suspended in 40.0 ml of N-methyl-2-pyrrolidinone, the suspension was cooled to 0° C., and 3.0 ml (1.5 equivalents) of cyclopropanecarbonyl chloride was added dropwise to the suspension. After the elapse of 4 hr from the dropwise addition, cyclopropanecarbonyl chloride (2.0 ml (1.0 equivalent)) was added dropwise thereto at 0° C.

A reaction was allowed to proceed at 0° C. for 69 hr, and the reaction solution was then poured into 100 ml of ethyl acetate and 120 ml of ice water and stirred, followed by separation. Ethyl acetate (100 ml) was added to the aqueous layer, the mixture was further neutralized with 9.5 g of sodium bicarbonate, and 8.0 g of sodium chloride was added thereto. The mixture was stirred and was allowed to stand, followed by separation. The organic layer was washed once with 30 ml of 5% brine and twice with 30 ml of water, and the mixture was concentrated under the reduced pressure. Ethyl acetate (35.0 ml) was added to the residue, and the mixture was then stirred at room temperature for 1.5 hr. Thereafter, 35.0 ml of n-hexane was added dropwise thereto over a period of two hr. The mixture was stirred at room temperature overnight. The precipitated crystals were then collected by filtration, were washed with 30 ml of n-hexane-ethyl acetate (1:1 (v/v)), and were dried under the reduced pressure for four hr to give 9.39 g of crystals containing 1,11-di-O-cyclopropanecarbonyl-1,7,11-trideacetylpyripyropene A. The crystals thus obtained were analyzed by the method described in Example 17 and were found to contain 1 mol of ethyl acetate based on 1.0 mol of 1,11-di-O-cyclopropanecarbonyl-1,7,11-trideacetylpyripyropene A (weight yield (as ethyl acetate solvate): 63.0%) (purity: 85.5%).

The powder X ray diffraction pattern of the crystals was in agreement with that in Example 17.

The ethyl acetate solvate (a 8.00 g portion in 9.39 g) of 1,11-di-O-cyclopropanecarbonyl-1,7,11-trideacetylpyripyropene A thus obtained was dissolved in 16.0 ml of methanol. The solution was heated to 35° C., and 10.0 ml of water was added. As a result, the solution became milky, and, hence, 1.0 ml of methanol was added thereto. After one hr from the addition of methanol, the mixture was cooled to 25° C., and a mixed solution composed of 16.8 ml of water and 7.2 ml of methanol was added dropwise thereto at 20 to 25° C. over a period of two hr. The mixture was stirred at room temperature overnight. The resultant precipitate was collected by filtration and was washed with a mixed solution composed of 7.0 ml of water and 3.0 ml of methanol. A sample (500 mg) was extracted from the solid thus obtained, and the remaining part was dried at 80° C. under the reduced pressure to give 5.68 g of 1,11-di-O-cyclopropanecarbonyl-1,7,11-trideacetylpyripyropene A (6.01 g when the amount of the extracted sample is taken into consideration) (total weight yield from 1,7,11-trideacetylpyripyropene A: 54.2%) (purity: 92.3%).

Example 19

Synthesis of 1,11-di-O-cyclopropanecarbonyl-1,7,11-trideacetylpyripyropene A 1,7,11-Trideacetylpyripyropene A (20.0 g) was suspended in 80.0 ml of N-methyl-2-pyrrolidinone, the suspension was cooled to −10° C., and 12.0 ml (3.0 equivalents) of cyclopropanecarbonyl chloride was added dropwise to the suspension. A reaction was allowed to proceed at −10° C. for 4 hr, and 4.0 ml (1.0 equivalent) of cyclopropanecarbonyl chloride was additionally added dropwise thereto. A reaction was then allowed to proceed at −10° C. for 72 hr, and the reaction solution was poured into 200 ml of ethyl acetate and 180 ml of 8% sodium bicarbonate water at 5° C. or below. The mixture was neutralized with 20 ml of 8% sodium bicarbonate water, 20 ml of 15% brine was then added, and the mixture was stirred at 10° C., followed by separation. The organic layer was washed thrice with 60 ml of water and was concentrated to 60 ml under the reduced pressure. Thereafter, 100 ml of ethyl acetate was added thereto, and the mixture was concentrated to 80 ml under the reduced pressure. The mixture was stirred at room temperature overnight, and the precipitated crystals were then collected by filtration and were washed with a mixed solution composed of 10 ml of n-hexane and 20 ml of ethyl acetate. The crystals thus obtained were dried under the reduced pressure at 80° C. overnight to give 17.80 g of 1,11-di-O-cyclopropanecarbonyl-1,7,11-trideacetylpyripyropene A. The crystals were analyzed by the method described in Example 17 and were found to contain 0.75 mol of ethyl acetate based on 1.0 mol of 1,11-di-O-cyclopropanecarbonyl-1,7,11-trideacetylpyripyropene A (weight yield: 61.8% (as ethyl acetate solvate)) (purity: 87.5%).

Example 20

Synthesis of 1,11-di-O-cyclopropanecarbonyl-1,7,11-trideacetylpyripyropene A 1,7,11-Trideacetylpyripyropene A (50.0 g) was suspended in 200 ml of N-methyl-2-pyrrolidinone, the suspension was cooled to −10° C., and 15.0 ml (1.5 equivalents) of cyclopropanecarbonyl chloride was added dropwise to the suspension. Thereafter, cyclopropanecarbonyl chloride was added, dropwise to the mixture, in an amount of 15.0 ml (1.5 equivalents) 3 hr after the dropwise addition and in an amount of 10.0 ml (1.0 equivalent) 5 hr after the dropwise addition at −10° C. A reaction was allowed to proceed at −10° C. for 72 hr. The reaction solution was then poured into 500 ml of ethyl acetate and 500 ml of 8% sodium bicarbonate water at 5° C. or below. The mixture was neutralized with a small amount of 8% sodium bicarbonate water, and 300 ml of 15% brine was added thereto at 10° C. or above, followed by separation. The organic layer was washed thrice with 100 ml of water and was concentrated to 150 ml under the reduced pressure. Thereafter, 250 ml of ethyl acetate was added thereto, and the mixture was again concentrated to 200 ml under the reduced pressure. Ethyl acetate (50 ml) was added thereto, and the mixture was stirred at room temperature overnight. The precipitated crystals were collected by filtration and were washed with 80 ml of ethyl acetate. The crystals thus obtained were dried under the reduced pressure at 50° C. for two hr to give 44.90 g of crystals containing 1,11-di-O-cyclopropanecarbonyl-1,7,11-trideacetylpyripyropene A. The crystals were analyzed by the method described in Example 17 and were found to contain 0.99 mol of ethyl acetate based on 1.0 mol of 1,11-di-O-cyclopropanecarbonyl-1,7,11-trideacetylpyripyropene A (weight yield: 60.2% (as ethyl acetate solvate)) (purity: 87.5%).

Example 21

Synthesis of 1,11-di-O-cyclopropanecarbonyl-1,7,11-trideacetylpyripyropene A 1,7,11-Trideacetylpyripyropene A (50.0 g) was suspended in 200 ml of N-methyl-2-pyrrolidinone, the suspension was cooled to −10° C., and 15.0 ml (1.5 equivalents) of cyclopropanecarbonyl chloride was added dropwise to the suspension. Thereafter, cyclopropanecarbonyl chloride was added, dropwise to the mixture, in an amount of 15.0 ml (1.5 equivalents) 3 hr after the dropwise addition and in an amount of 10.0 ml (1.0 equivalent) 5 hr after the dropwise addition at −10° C. A reaction was allowed to proceed at −10° C. for 75 hr. The reaction solution was then poured into a mixed solution composed of 500 ml of ethyl acetate, 500 ml of ice water, and 40.0 g of sodium bicarbonate at 5° C. or below. The mixture was neutralized with a small amount of 8% sodium bicarbonate water and 300 ml of 15% brine was added at 10° C. or above, followed by separation. The organic layer was washed thrice with 150 ml of water and was concentrated to 100 ml under the reduced pressure. Thereafter, 200 ml of ethyl acetate was added thereto, and the mixture was again concentrated to 150 ml under the reduced pressure. Further, 50 ml of ethyl acetate was then added thereto, and the mixture was stirred at room temperature overnight. The precipitated crystals were collected by filtration and were washed with 60 ml of ethyl acetate. The crystals thus obtained were dried under the reduced pressure at 40° C. for one hr and were dried at room temperature for two hr to give 49.10 g of crystals containing 1,11-di-O-cyclopropanecarbonyl-1,7,11-trideacetylpyripyropene A (weight yield: 65.8% (as ethyl acetate solvate)) (purity: 84.7%).

The crystals were analyzed in the same manner as in Example 17 and were found to contain 0.98 mol of ethyl acetate based on 1.0 mol of 1,11-di-O-cyclopropanecarbonyl-1,7,11-trideacetylpyripyropene A.

A 24.0 g portion in the crystals thus obtained was suspended in 48.0 ml of ethyl acetate, and the suspension was stirred at 70° C. for one hr and was stirred at room temperature overnight. Thereafter, the reaction solution was filtered, followed by washing with 30 ml of ethyl acetate. The washed product was dried at room temperature for 5 hr to give 20.54 g of the contemplated product (weight yield: 56.4% (as ethyl acetate solvate; total yield from 1,7,11-trideacetylpyripyropene A) (purity: 93.2%).

The crystals thus obtained contained 1.00 mol of ethyl acetate based on 1.0 mol of 1,11-di-O-cyclopropanecarbonyl-1,7,11-trideacetylpyripyropene A.

Example 22

1,11-O-dicyclopropanecarbonyl-1,7,11-trideacetylpyripyropene A was synthesized from 1,7,11-O-tricyclopropanecarbonyl-1,7,11-trideacetylpyripyropene A synthesized in Example 8 under reagent, solvent, time, and temperature conditions described in Table 3 below. After the completion of the reaction, the reaction solution was analyzed by high-performance liquid chromatography under the following analytical conditions to determine the amount of 1,11-O-dicyclopropanecarbonyl-1,7,11-trideacetylpyripyropene A produced in the reaction solution. The results are shown in Table 3.

Analytical Conditions

Detector: Ultraviolet absorptiometer or photodiode array detector (measuring wavelength: 254 nm)

Column: CAPCELL PAK C18; 2.0 mm I.D×150 mm inner diameter; 5 µm

Column temp.: 40° C.

Mobile phase A: Water

Mobile phase B: Acetonitrile for liquid chromatography

Feed of mobile phase: Concentration gradient is regulated by varying the mixing ratio between mobile phase A and mobile phase B as follows.

Flow rate: 0.2 mL/min

Conditions for mobile phase: As shown in Table 2 below

TABLE 2

| Time after injection (min.) | Mobile phase A (vol %) | Mobile phase B (vol %) |
|---|---|---|
| 0 to 1 min | 70 | 30 |
| 1 to 20 min | 70 → 0 | 30 → 100 |
| 20 to 24 min | 0 | 100 |

TABLE 3

| Reagent (number of equivalents) | Solvent | Time | Temp. | Area % | Isolation yield |
|---|---|---|---|---|---|
| DBU (1.1) | MeOH—H2O (4:1) | 21 h | r.t. | | 39% |
| DBN (1.1) | MeOH—H2O (4:1) | 15 h | r.t. | | 45% |
| Na2CO3 (1.1) | MeOH—H2O (9:1) | 15 h | r.t. | | 37% |
| K2CO3 (0.5) | MeOH—H2O (19:1) | 16 h | r.t. | 48% | 38% |
| t-BuOK (0.5) | MeOH—H2O (19:1) | 16 h | r.t. | 50% | 41% |
| KHCO3 (1⇒24) | MeOH—H2O (4:1) | 14 d | r.t. | | 47% |
| NaHCO3 (1⇒24) | MeOH—H2O (4:1) | 14 d | r.t. | | 45% |
| 0.05M NaOMe (1.0) | MeOH | 2 h | 50° C. | | 42% |
| 1M NaOH (1.0) | MeOH | 2 h | 50° C. | | 46% |
| 0.01M NaOMe (1.0) | MeOH | 2 d | r.t. | | 49% |

TABLE 3-continued

| Reagent (number of equivalents) | Solvent | Time | Temp. | Area % | Isolation yield |
|---|---|---|---|---|---|
| K2CO3 (2⇒14) | MeOH | 6 h | r.t. | | 50% |
| Cs2CO3 (2.0) | MeOH | 24 h | r.t. | | 50% |
| 0.1M LiOH (1.0) | MeOH—H2O (9:1) | 19 h | r.t. | | 33% |
| 0.1M CsOH (1.0) | MeOH—H2O (9:1) | 19 h | r.t. | | 32% |
| Cs2CO3 (0.1) | MeOH—THF (3:2) | 15 h | r.t. | | 34% |
| K2CO3 (0.2) | MeOH—CHCl3 (3:2) | 45 h | r.t. | | 31% |
| K2CO3 (0.5) | MeOH | 13 h | r.t. | | 44% |
| Cs2CO3 (0.5) | MeOH | 13 h | r.t. | | 45% |

The invention claimed is:
1. A process for producing a compound C represented by formula C:

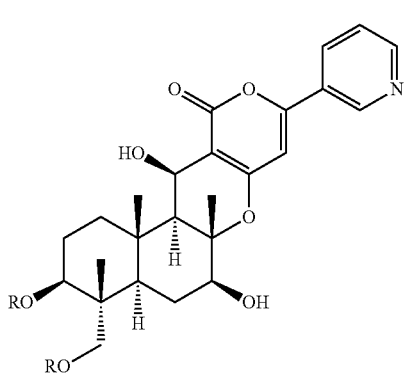

wherein R represents a straight chain, branched chain, or cyclic $C_{2-6}$ alkylcarbonyl, provided that, when the alkyl moiety in the alkylcarbonyl group is of a branched chain or cyclic type, then R represents $C_{3-6}$ alkylcarbonyl, the process comprising:
selectively acylating hydroxyl groups at the 1-position and 11-position of a compound B1 represented by formula B1:

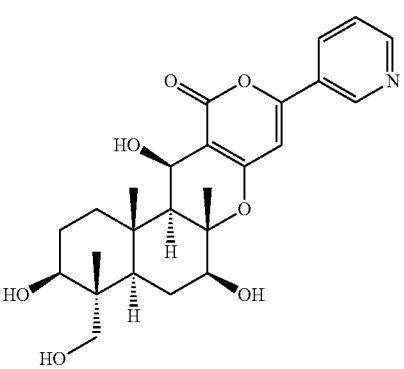

with an acylating agent in an amount of 2.0 to 5.0 equivalents based on the amount of the compound B1, through one to three steps in the presence or absence of a base, in an aprotic polar organic solvent selected from the group consisting of N,N-dimethylformamide, dimethylsulfoxide, N,N-dimethylacetamide, acetonitrile, N-methyl-2-pyrrolidinone, N-methyl-2-piperazinone and N,N-dimethyl-2-imidazolidinone,
to obtain the compound C.

2. The process according to claim 1, wherein the compound C is produced by acylating the hydroxyl groups at the 1-position and 11-position of the compound B1 through one step.

3. The process according to claim 1, which comprises producing the compound C by acylation through two steps consisting of the steps of:
acylating a hydroxyl group at the 11-position of the compound B1 with an acylating agent to give a compound B2 represented by formula B2:

[Chemical formula 3]

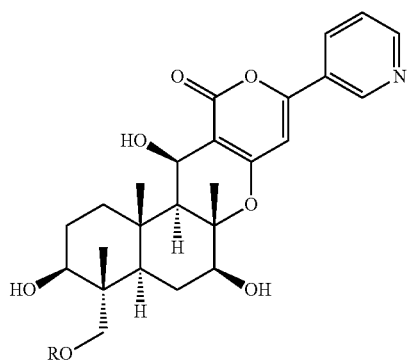

B2 wherein R is as defined in formula C in claim 1; and
further acylating a hydroxyl group at the 1-position of the compound B2.

4. The process according to claim 1, which comprises producing the compound C by acylation through three steps consisting of the steps of:
acylating a hydroxyl group at the 11-position of the compound B1 to give a compound B2 represented by formula B2:

[Chemical formula 4]

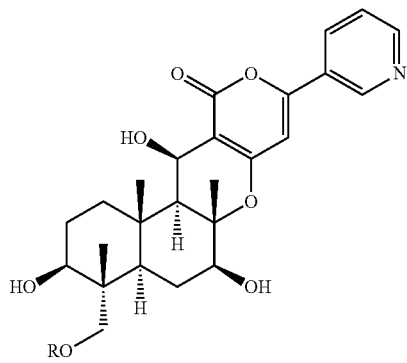

B2 wherein R is as defined in formula C in claim 1;
transferring acyl at the 11-position of the compound B2 to a hydroxyl at the 1-position to give a compound B3 represented by formula B3:

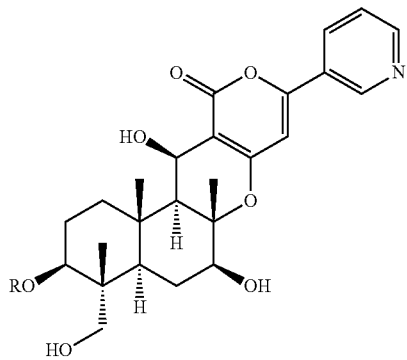

B3 wherein R is as defined in formula C in claim 1; and
acylating a hydroxyl group at the 11-position of the compound B3.

5. The process according to claim 1, which further comprises, as a step of producing the compound B1, hydrolyzing acyl groups at the 1-position, 7-position, and 11-position of a compound A1 represented by formula A1:

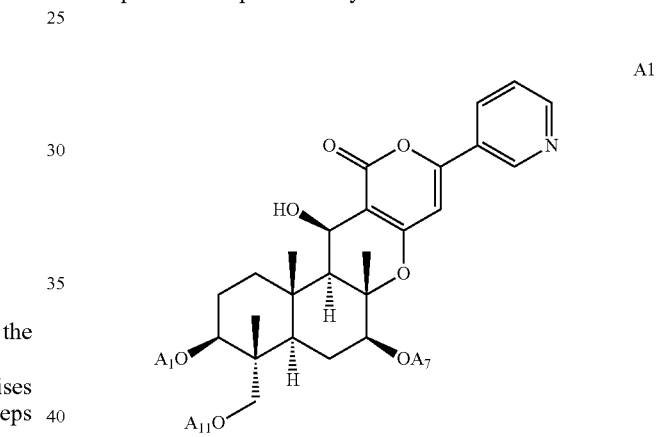

A1 wherein $A_1$, $A_7$, and $A_{11}$, which may be the same or different, represent acetyl or propionyl,
in the presence of a base.

6. The process according to claim 1, wherein the acylation is carried out in the absence of a base.

7. The process according to claim 1, wherein the base used in acylating the hydroxyl at the 1-position and/or 11-position of the compound B1 is 2,4,6-collidine or 2,6-lutidine.

8. The process according to claim 3, wherein the base is used in the step of producing the compound B2 and in the step of further acylating the hydroxyl at the 1-position of the compound B2, and wherein the amount of the base used in the step of producing the compound B2 is 1.0 to 3.0 equivalents based on the compound B1, and the total amount of the base used in the step of producing the compound B2 and the base used in the step of further acylating the hydroxyl at the 1-position of the compound B2 is 2.0 to 4.5 equivalents.

9. The process according to claim 3, wherein the acylating agent is used in the step of producing the compound B2 and in the step of further acylating the hydroxyl at the 1-position of the compound B2, and wherein the amount of the acylating agent used in the step of producing the compound B2 is 1.0 to 3.5 equivalents based on the compound B1, and the total amount of the acylating agent used in the step of producing the compound B2 and the acylating agent used in the step of further acylating the hydroxyl at the 1-position of the compound B2 is 2.0 to 4.5 equivalents.

10. The process according to claim 1, wherein R represents cyclopropanecarbonyl.

11. The process according to claim 4, wherein the step of producing the compound B3 from the compound B2 is carried out in the presence of a base.

12. The process according to claim 1, which further comprises a step of isolating and purifying the compound C from a reaction solution comprising the compound C by crystallization.

* * * * *